(12) United States Patent
Pettit et al.

(10) Patent No.: US 7,462,609 B2
(45) Date of Patent: Dec. 9, 2008

(54) NARCISTATIN PRODRUGS

(75) Inventors: George R. Pettit, Paradise Valley, AZ (US); Noeleen Melody, Mesa, AZ (US)

(73) Assignee: Arizona Board of Regents, Tempe, AZ (US)

( * ) Notice: Subject to any disclaimer, the term of this patent is extended or adjusted under 35 U.S.C. 154(b) by 264 days.

(21) Appl. No.: 10/537,968

(22) PCT Filed: Dec. 9, 2003

(86) PCT No.: PCT/US03/39067

§ 371 (c)(1),
(2), (4) Date: Jun. 9, 2005

(87) PCT Pub. No.: WO2004/052298

PCT Pub. Date: Jun. 24, 2004

(65) Prior Publication Data

US 2006/0135481 A1    Jun. 22, 2006

Related U.S. Application Data

(60) Provisional application No. 60/432,219, filed on Dec. 9, 2002.

(51) Int. Cl.
A61K 31/675 (2006.01)
C07F 9/06 (2006.01)
(52) U.S. Cl. ............... 514/80; 546/23; 546/65
(58) Field of Classification Search ........... 546/23, 546/65; 514/80
See application file for complete search history.

(56) References Cited

U.S. PATENT DOCUMENTS

| | | | |
|---|---|---|---|
| 4,522,811 A | 6/1985 | Eppstein et al. | 514/2 |
| 5,529,989 A | 6/1996 | Pettit et al. | 514/81 |
| 5,830,850 A | 11/1998 | Gelb et al. | 514/2 |
| 5,985,436 A | 11/1999 | Hirokane et al. | 514/287 |
| 7,067,480 B2 | 6/2006 | Harnett et al. | 514/8 |

FOREIGN PATENT DOCUMENTS

| JP | 11255650 | 9/1999 |
|---|---|---|
| WO | WO/2000/048606 | 8/2000 |

OTHER PUBLICATIONS

International Search Report for International Application No. PCT/US03/39067 dated Mar. 25, 2004.
Pettit et al., "Antineoplastic Agents 500. Narcistatin", J. Nat. Prod., 66:92-96, 2003.
Pettit et al., "Antineoplastic Agents. 450. Synthesis of (+)-Pancratistatin from (+)-Narcilasine as Relay $1^{\alpha}$", J. Org. Chem., 66:2583-2587 (2001).
Khaldi et al., "A Short Route to Enantiomerically Pure Narciclasine Derivatives", Tetrahedron Letters, 17:3003-3006 (1995).
Veronese et al., "Slow Release of Narciclasine from Matrices Obtained by Radiation-Induced Polymerization", Journal of Controlled Release, 16:291-298 (1991).
Supplementary European Search Report for EP Application No. EP 03 81 2894 dated Jul. 25, 2007.
Ackerman et al., "Effects of Naproxen on Connective Tissue Changes in the Adjuvant Arthritic Rat", Arthritis and Rheumatism, 22(12):1365-1374 (1979).
Afuwape et al., "The Role of the Angiogenic Molecule VEGF in the Pathogenesis of Rheumatoid Arthritis", Histol. Histophathol., 17(6):961-972 (2002).
Afuwape et al., "Adenoviral Delivery of Soluble VEGF Receptor 1 (sFlt-1) Abrogates Disease Activity in Murine Collagen-Induced Arthritis", Gene Ther., 10:1950-1960 (2003).
Allen et al., "Suppression of Monocyte Function and Differential Regulation of IL-1 and IL-1ra by IL-4 Contribute to Resolution of Experimental Arthritis", J. Immunol., 151(8):4344-4351 (1993).
Berge et al., "Pharmaceutical Salts", J. Pharm. Sci., 66(1):1-19 (1997).
Borderie et al., "Nitric Oxide Synthase is Expressed in the Lymphomononuclear Cells of Synovial Fluid in Patients with Rheumatoid Arthritis", The Journal of Rheumatology, 26(10):2083-2088 (1999).
Bresnihan et al., "Microscopic Measurement of Synovial Membrane Inflammation in Rheumatoid Arthritis: Proposals for the Evaluation of Tissue Samples by Quantitative Analysis", Br J Rheumatol, 37:636-642 (1998).
Burmester et al., "Mononuclear Phagocytes and Rheumatoid Synovitus. Mastermind or Workhorse in Arthritis", Arthritis Rheum. 40(1):5-18 (1997).
Camilleri et al., "The Effect of Free and Lipsome-Encapsulated Clodronate on the Hepatic Mononuclear Phagocyte System in the Rat", Clin. Exp. Immunol, 99:269-275 (1995).

(Continued)

Primary Examiner—Rei-Tsang Shiao
(74) Attorney, Agent, or Firm—Fennemore Craig, P.C.

(57) ABSTRACT

The present invention provides prodrugs derived from the sparingly soluble anticancer isocarbostyril narciclasine, a component of various Narcissus species, said prodrugs having potential for use against animal and human cancers. Also disclosed is an efficient procedure for the synthetic conversion of narciclasine to several more soluble cyclic phosphate compounds, including "narcistatin".

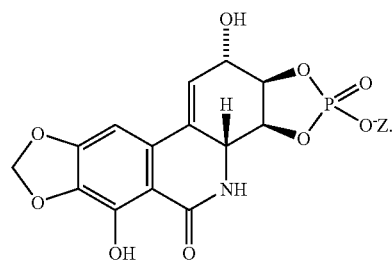

3 Claims, 2 Drawing Sheets

OTHER PUBLICATIONS

Carol et al., "Immunohistochemical Study of Lymphoid Tissues in Adjuvant Arthritis (AA) by Image Analysis; Relationship with Synovial Lesions", *Clin. Exp. Immunol*, 120:200-208 (2000).

Dijkstra et al., "Macrophages and Dendritic Cells in Antigeninduced Arthritis: An Immunohistochemical Study Using Cryostat Sections of the Whole Knee Joint of Rat", *Scand J. Immunol*, 26:513-523 (1987).

Edmonds et al., "Antirheumatic Drugs: A Proposed New Classification", *Arthritis Rheum*, 36(3):336-339 (1993).

Egeland, T., "Immunological Aspects of the Rheumatoid Synovium", *scand J. Rheumatol Suppl.* 66:27-33 (1987).

Feldmann et al., "Role of Cytokines in Rheumatoid Arthritis", *Annu. Rev. Immunol*, 14:397-440 (1996).

Feldmann et al., "Anti-TNFα Therapy of Rhuematoid Arthritis: What Have We Learned?", *Ann. Rev. Immunol*, 19:163-196 (2001).

Firestein et al., "Anticytokine Therapy in Rheumatoid Arthritis", *N. Engl. J. Med.* 337(3):195-197 (1997).

Fox, DA., "The Role of T Cells in the Immunopathogenesis of Rheumatoid Arthritis: New Perspectives", *Arthritis Rheum*, 40(4):598-609 (1997).

Gabrielson et al., "Antivral (RNA) Activity of Selected Amaryllidaceae Isoquinoline Constituents and Sythesis of Related Substances", *J. Natural Products*, 55(11):1569-1581 (1992).

Giatromanolaki et al., "The Angiogenic Pathway 'Vascular Endothelial Growth Factor/FLK-I (KDR)- receptor' in Rheumatoid Arthritis and Osteoarthritis", *J. of Pathology*, 194(1):101-108 (2001).

Hudlicky et al., "Total Synthesis and Biological Evaluation of Amaryllidaceae Alkaloids: Narciclasine, ent-7-deoxypancratistatin Regioisomer of 7-Deoxypancratistatin, 10b-epi-deoxypancratistatin, and Truncated Derivatives", *J. Org. Chem.*, 67:8726-8743 (2002).

Idso et al., "Effects of Atomosperic $CO_2$ Enrichment on the Growth and Development of *Hymenocallis Littoralis* (Amaryllidaceae) and the Concentrations of Several Antineplastic and Antiviral Constituents of its Bulbs", *Am. J. Bot.*, 87(6):769-773 (2000).

Keffer et al., "Transgenic Mice Expressing Human Tumor Necrosis Factor: A Predictive Genetic Model of Arthritis", *EMBO J.*, 10(13):4025-4031.

Kinne et al., "Treatment of Rat Arthritides with Clodronate-Containing Liposomes", *Scand. J. Rheumatol Suppl.*, 24(101):91-97 (1995).

Kinne et al., "Long-Term Amelioration of Rat Adjuvant Arthritis Following Systemic Elimination of Macrophages by Clodronate-Containing Liposomes", *Arthritis Rheum*, 38(12):1777-1790 (1995).

Kool et al, "Immunohistology of Joint Inflammation Induced in Rats by Cell Wall Fragments of Eubacterium Aerofaciens", *Scand J. Immunol*, 36:497-506 (1992).

Lala et al., "Role of Nitric Oxide in Carcinogenesis and Tumour Progression", *Lancet Oncol.*, 2(3) 149-156 (2001).

Lavastre et al., "anti-Inflammatory Effect of Viscum Album Agglutinin-1 (VAA-1): Induction of Apoptosis in Activated Neutrophils and Inhibition of Lipopolysaccharide-Induced Neutrophilic Inflammation in Vivo", *Clin. Exp. Immunol*, 137:272-278 (2004).

Lorton et al., "Norepinephrine Content in Primary and Secondary Lymphoid Organs is Altered in Rats with Adjuvant-Induced Arthritis", *Mech Ageing Dev.*, 94:145-163 (1997).

Lu et al., "Vascular Endothelial Growth Factor Expression and Regulation of Murine Collagen-Induced Arthristis", *J. Immunol*, 164(11):5922-5927 (2000).

McNulty et al., "Studies Directed Towards the Refinement of the Pancratistatin Cytotoxic Pharmacophore", *BioOrganic & Medicinal Chemistry Letters*, 11:169-172 (2001).

Mikami et al., "Suppressive Activity of Lycoricidinol (Narciclasine) Against Cytotoxicity of Neutrophil-Derived Calprotectin, and its Suppressive Effect on Rat Adjuvant Arthritis Model", *Biol Pharm Bull*, 22(7):674-678 (1999).

Mulherin et al., "Synovial Tissue Macrophage Populations and Articular Damage in Rheumatoid Arthritis", *Arthritis Rheum*, 39(1):115-124 (1996).

Mulherin et al., "Clinical Improvement and Radiological Deterioration in Rheumatoid Arthritis: Evidence that the Pathogenesis of Synovial Inflammation and Articular Erosion May Differ", *Br. J. Rheumatology*, 35:1263-1268 (1996).

Nandakumar et al., "Collagen Type II-Specific Monoclonal Antibody-Induced Arthritis in Mice", *AJP*, 163(5):1827-1837 (2003).

Ouarzane-Amara et al., "In Vitro Activities of two Antimitotic Compounds, Pancratistatin and 7-Deoxynarciclasine, Against *Encephalitozoon Intestinals*, a Microsporidium Causing Infections in Humans", *Antimicrob Agents Chemother*, 45(12):3409-3415 (2001).

Paleolog et al., "Angiogenesis in Arthritis: Role in Disease Pathogenesis and as a Potential Therapeutic Target", *Angiogenesis*, 2(4):295-307 (1998).

Paleolog et al., "Angiogenesis in Rheumatoid Arthritis", *Arthritis Res.*, 4(3):S81-90 (2002).

Pettit et al., "Synthesis of 10b-(R)-hydroxy-pancratistatin via narciclasine", *J. Chem Soc., Chem Commun.*, 2725-2726 (1994).

Pettit et al., "Antineplastic Agents. 500. Narcistatin", *J. Nat. Prod.*, 66(1):92-96 (2003).

Pettit et al., "Antineoplastic Agents, 294. Variations in the formation of pancratistatin and related isocarbostyrils in *Hymenocallis Littoralis*", *J. Nat. Prod.*, 58(1):37-43 (1995).

Pettit et al., "Antineoplastic Agents, 256. Cell Growth Inhibitory Isocarbostyrils from *Hymenocallis*", *J. Nat. Prod.*, 56(10):1682-1687 (1993).

Pettit et al., "Chapuis J-C Synthesis of 10b(R)-hydroxypancratistatin, 10b(S)-hydroxy-1-epipancratistatin, 10b(S)-hydroxy-1,2-diepipancratistatin and related isocarbostyrils", *Heterocycles*, 56:139-155 (2002).

Pettit et al., "Antineoplastic Agents. 511. Direct Phosphorylation of Phenpanstatin and Pancratistatin[tr]", *J. Nat. Prod.*, 67:322-327 (2004).

Pettit et al., "Antineoplastic Agents. 453. Synthesis of Pancratistatin Prodrugs", *Anti-Cancer Drug Design.*, 15:389-395 (2000).

Pettit et al., "Antineoplastic Agents. 120. Pancratium Littorale", *J. Nat. Prod.*, 49(6):995-1002 (1986).

Pettit et al., "Antineoplastic Agents, 301. An Investigation of the Amaryllidaceae Genus *Hymenocallis*", *J. Nat. Prod.*, 58(5):756-759 (1995).

Richards et al., "Liposomal Clodronate Eliminates Synovial Macrophages, Reduces Inflammation and Ameliorates Joint Destruction in Antigen-Induced Arthritis", *Rheumatology*, 38:818-825 (1999).

Rojas et al., "ttCH, a Selective Inhibitor of Inducible Nitric Oxide Synthase Expression with Antiarthritic Properties", *Eur. J. Pharmacol*, 465:183-189 (2003).

Rojas et al., "Therapeutic Administration of 3,4,5-trimethoxy-4'-Fluorochalcone, A Selective Inhibitor of iNOS Expression, Attenuates the Development of Adjuvant-Induced Arthritis in Rats", *Naunyn Schmiedebergs Arch Pharmacol*, 368:225-233 (2003).

Sidwell et al., "Antiviral and Immunomodulating Inhibitors of Experimentally-Induced Punta Toro Virus Infections", *Antiviral Research, Elsevier Science BV*, 25(2):105-122 (1994).

Sone et al., "Elevated Levels of Vascular Endothelial Growth Factor in the Sera of Patients with Rheumatoid Arthritis Correlation with Disease Activity", *Life Sci.*, 69(16):1861-1869 (2001).

Veronese et al., "In Vitro and in Vivo Behavior of Narciclasine released from Matrices Based on Poly (2-hydroxyethyl Methacrylate)", *IL Farmaco*, 46(9):1061-1070 (1991).

Verschure et al., "Macrophages and Dendritic Cells During the Early Stages of Antigen-Induced Arthritis in Rats: Immunohistochemical Analysis of Cryostat Sections of the Whole Knee Joint", *Scand J. Immunol*, 29:371-381 (1989).

Williams et al., "Anti-Tumor Necrosis Factor Ameliorates Joint Disease in Murine Collagen-Induced Arthritis", *Proc. Natl. Acad. Sci. USA*, 89:9784-9788 (1992).

Yonekura et al., "Association Between the Expression of Inducible Nitric Oxide Synthase by Chondrocytes and its Nitric Oxide-Generating Activity in Adjuvant Arthritis in Rats", *Nitric Oxide*, 8:164-169 (2003).

Yui et al., "Inhibition Effect of Amaryllidaceae Alkaloids, Lycorine and Lycoricidinol on Macrophage TNF-Alpha Production", *Yakugaku Zasshi*, 121:168-171 (2001).

NARCISTATIN PRODRUGS

RELATED APPLICATION DATA

This application is the U.S. national stage of PCT/US03/39067 filed on Dec. 9, 2003, which is based on and claims the benefit of U.S. Provisional Patent Application No. 60/432,219 filed on Dec. 9, 2002, which is incorporated herein in its entirety by this reference.

INTRODUCTION

Financial assistance for this invention was provided by the United States Government, Division of Cancer Treatment and Diagnosis, National Cancer Institute, Department of Health and Human Services, Outstanding Investigator Grant CA44344-03-12 and CA90441-01; the Arizona Disease Control Research Commission; and private contributions. Thus, the United States Government has certain rights in this invention.

FIELD OF THE INVENTION

This invention relates to a novel compounds, and methods for synthesizing same, which show promising utility in the treatment of cancer. The compound described herein has been denominated narcistatin. Further described herein are numerous derivatives of narcistatin.

BACKGROUND OF THE INVENTION

Over 30 species representing 11 genera (among 85 total) of the plant family Amaryllidaceae have been employed in traditional treatments for human cancer. Such applications of certain *Narcissus* species were recorded as early as 200 B.C. (Pettit, G. R. et al., *J. Nat. Prod.* 1995, 58, 756-759; Pettit, G. R., et al., *J. Nat. Prod.*, 1995, 58, 37-43.) The biologically active constituents of Amaryllidaceae species have been under investigation from at least 1877 following Gerrard's report on a component of Narcissus pseudonarcissus designated narcissia. (Gerrard, A. W., *Pharm. J.*, 1877, 8, 214; Cook, J. W., In *The Alkaloids*, Manske, R. H. F.; Holmes, H. L., Ed.; Academic Press: New York, 1952; pp. 331.) Presently, some 48 alkaloids and carbostyrils bearing a variety of carbon skeletons have been isolated from Narcissus species. (Weniger, B., et al., *Planta Med.*, 1995, 61, 77-79.) Of these, the isocarbostyrils narciclasine (1) and pancratistatin (2) have been found to display the most promising in vivo antineoplastic activities and a selection of other amaryllidaceae alkaloids have been shown to provide cancer cell growth inhibitory activity. (Pettit, G. R., et al., *J. Nat. Prod.*, 1995, 58, 756-759; Pettit, G. R., et al., *J. Nat. Prod.*, 1995, 58, 37-43; Pettit, G. R., et al., *J. Org. Chem.*, 2001, 66, 2583-2587; Rigby, J. H., et al., *J. Amer. Chem. Soc.*, 2000, 122, 6624-6628; Suffness, M., et al., In The Alkaloids, Drossi, A., Ed., Academic Press: New York, 1985; pp. 205-207; Youssef, D. T. A., et al., Pharmazie 2001, 56, 818-822.)

Pancratistatin (2), which we first discovered in *Pancratium littorale* (reidentified as *Hymenocallis littoralis*) and later in *Narcissus* species, has been undergoing extended preclinical development. (Pettit, G. R., et al., *J. Org. Chem.*, 2001, 66, 2583-2587; Rigby, J. H., et al., *J. Amer. Chem. Soc.* 2000, 122, 6624-6628; Pettit, G. R., et al., *J. Nat. Prod.*, 1995, 58, 756-759; Pettit, G. R., et al., *J. Nat. Prod.*, 1995, 58, 37-43.) That very important initiative was greatly assisted by conversion of the sparingly soluble isocarbostyril to a 7-O-phosphate salt. (Pettit, G. R., et al., *Anti-Cancer Drug Design* 2000, 15, 389-395; Pettit, G. R., et al., *Anti-Cancer Drug Design* 1995, 10, 243-250.) The antimitotic activity of narciclasine (1) has been known for over 35 years. Subsequently, it was shown in U.S. National Cancer Institute research to be active against in vivo growth of the M5076 sarcoma and P388 lymphocytic leukemia. In addition, it was found to inhibit protein synthesis in Erlich asciter cancer cells. (Suffness, M., et al., The Alkaloids, Drossi, A., Ed., Academic Press: New York, 1985; pp. 205-207.) However, as with the closely related pancratistatin (2), the low solubility properties of narciclasine has contributed to the delay in its preclinical development. Most of the inventors' early investigation involving this potentially useful isocarbostyril have targeted its use as a starting point for a practical synthesis of pancratistatin (2) and for SAR purposes. (Pettit, G. R., et al., *J. Org. Chem.* 2001, 66, 2583-2587; Rigby, J. H., et al., *Amer. Chem. Soc.* 2000, 122, 6624-6628; Pettit, G. R., et al., *J-C. Heterocycles* 2002, 56, 139-155.) Disclosed herein a very convenient transformation of narciclasine (1) to water soluble cyclic phosphate prodrugs (3).

SUMMARY OF THE INVENTION

Disclosed herein are several derivatives of narciclasine, and methods for the synthesis of these derivatives. The compounds of the invention have the following structure:

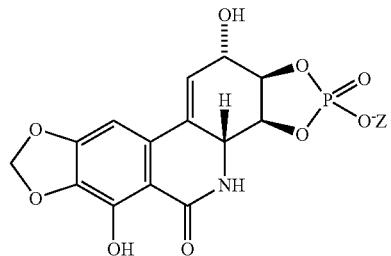

Compound 3a: Z=pyridinium
Compound 3b: Z=H$^+$
Compound 3c: Z=Li$^+$
Compound 3d: Z=Na$^+$
Compound 3e: Z=K$^+$
Compound 3f: Z=Cs$^+$
Compound 3g: Z=M$^{2+}$
Compound 3h: Z=Ca$^+$
Compound 3i: Z=Zn$^{2+}$
Compound 3j: Z=Mn$^{2+}$
Compound 3k, Z=quinidine
Compound 3l: Z=quinine
Compound 3m: Z=imidazole
Compound 3n: Z=morpholine
Compound 3o: Z=piperazine Narcistatin (3b) and fifteen salt derivatives were evaluated against a panel of human cancer cell lines and the range (0.1-0.01) of GI$_{50}$ values in μg/ml was found to parallel that shown by the parent narciclasine, and thus indicates that the compounds of the present invention show promise in the treatment of cancer in humans and animals. The water-soluble cyclic phosphate prodrugs disclosed herein will allow the potentially useful *Narcissus* anticancer component narciclasine to be utilized in cancer-fighting pharmaceuticals.

Also disclosed herein is a method for the efficient synthetic conversion of the sparingly soluble anticancer compound isocarbostyril narciclasine (1), a component of various *Narcissus* species, to a more soluble cyclic-phosphate designated narcistatin (3b). The reaction between narciclasine, tetrabutylammonium dihydrogen phosphate, dicyclohexylcarbodiimide, and p-toluenesulfonic acid in pyridine afforded pyridinium narcistatin (3a) in reasonable yields. Preparation of sodium narcistatin (3d) was achieved by two methods. Procedure A involved the transformation of narcistatin (3a) into the water soluble prodrug (3d) and other salt derivatives by cation exchange chromatography. Procedure B allowed sodium narcistatin (3d) to be obtained in high yield, following cation exchange chromatography, from the reaction between narciclasine, tetrabutylanimonium dihydrogen phosphate and dicyclohexylcarbodiimide in pyridine.

DETAILED DESCRIPTION OF THE INVENTION

Early experience by one of the inventors in nucleotide chemistry involving phosphate esters and cellular phosphatases combined with recent successes in synthesis of phosphate prodrugs made such an approach most attractive for obtaining a water soluble narciclasine prodrug. (Pettit, G. R. Synthetic Nucleotides, Van Nostrand Reinhold Co: New York, 1972; Pettit, G. R., et al., Anti-Cancer Drug Design 2000, 15, 389-395; Pettit, G. R., et al., Anti-Cancer Drug Design 1995, 10, 243-250; Pettit, G. R., et al., Anti-Cancer Drug Design 2000, 15, 397-403; Saulnier, M. G., et al., Med. Chem. Lett. 1994, 4, 2567-2572; Ueda, Y., et al., Med. Chem. Lett. 1995, 5, 247-252.) However, a selection of the more obvious methods such as $PCl_3$, or 2-cyanoethylphosphate with dicyclohexylcarbodiimide (DCCI), and various unprotected or protected (e.g. narciclasine 3,4-acetonide) strategies involving narciclasine (1) led to unpromising mixtures. (Pettit, G. R., et al., Anti-Cancer Drug Design 2000, 15, 389-395; Pettit, G. R., et al., Anti-Cancer Drug Design 1995, 10, 243-250; Taktakishvili, M., et al., Tetrahedron Lett. 2000, 41, 7173-7176; Tener, G. M., J. Amer. Chem. Soc. 1961, 83, 159-168; Scheit, K. H., Nucleotide Analogs, Synthesis and Biological Function; Wiley-Interscience: New York, 1972; Khorana, H. G., et al., J. Chem. Soc. 1953, 2257-2260; Khorana, H. G. J. Amer. Chem. Soc. 1954, 76, 3517-3527; Dekker, C. A., et al., J. Amer. Chem. Soc. 1954, 76, 3522-3527; Tener, G. M.; Khorana, H. G., J. Amer. Chem. Soc. 1955, 77, 5348.) Eventually, the inventors examined use of the readily soluble tetrabutylammonium dihydrogen phosphate in pyridine as the phosphate source. Initially, the phosphate failed to couple with narciclasine in the presence of DCCI until three equivalents of p-toluenesulfonic acid was employed to promote condensation, at which point precipitation of dicyclohexylurea (DCU) began. When the reaction mixture was heated to 80° C., the pyridinium salt of narciclasine-3,4-cyclic phosphate 3a (herein designated pyridinium narcistatin), precipitated. Following collection of precipitated DCU and the narcistatin pyridinium salt, the solids were titrated with water to dissolve the cyclic phosphate (3a). Concentration of the water fraction afforded the pyridinium salt in 40% yield. The mother liquor was concentrated to a brown oil and added to a large volume of water; an immediate precipitate was observed. The solution was filtered and the filtrate was found to be primarily unreacted narciclasine with some DCU as impurity. The reaction did not go to completion even after prolonged stirring and addition of more reagents.

Figure 1:
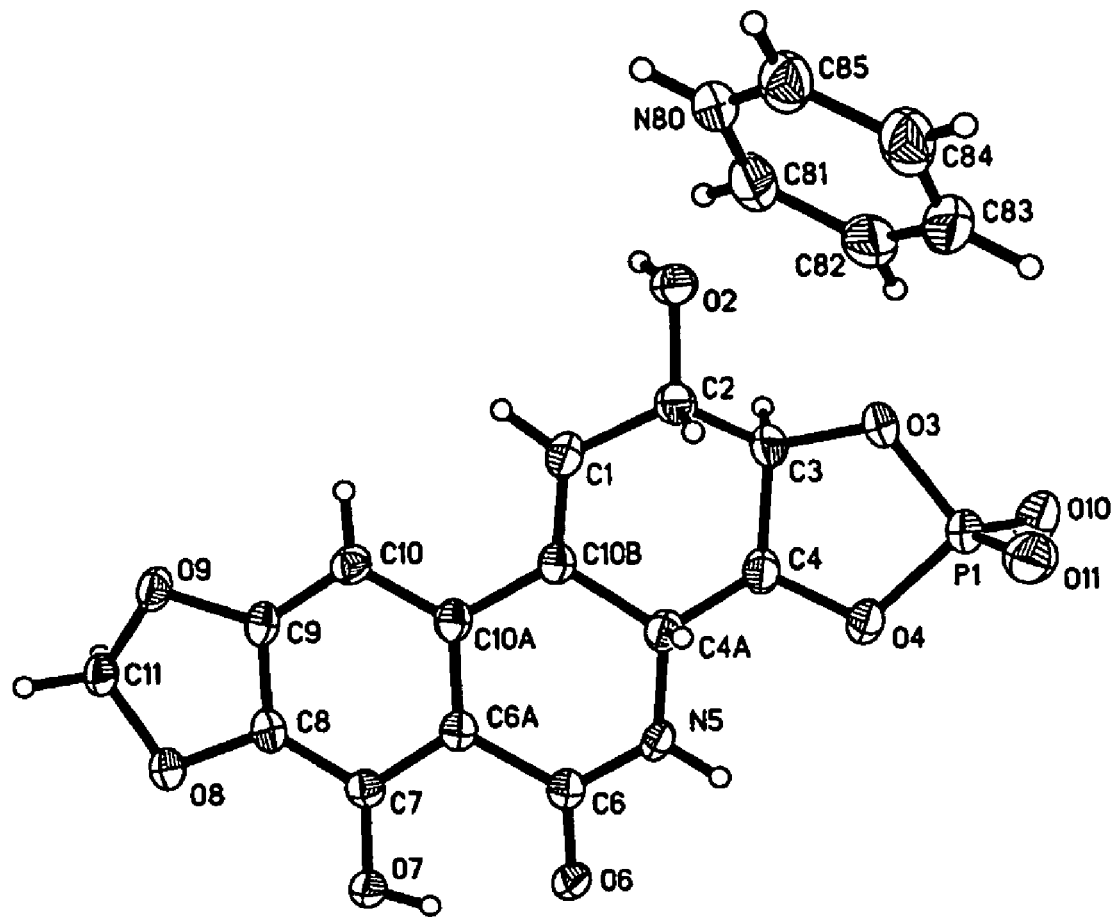
FIG. 1 illustrates the x-ray structure of pyridinium narcistatin (3a).
Figure 2:
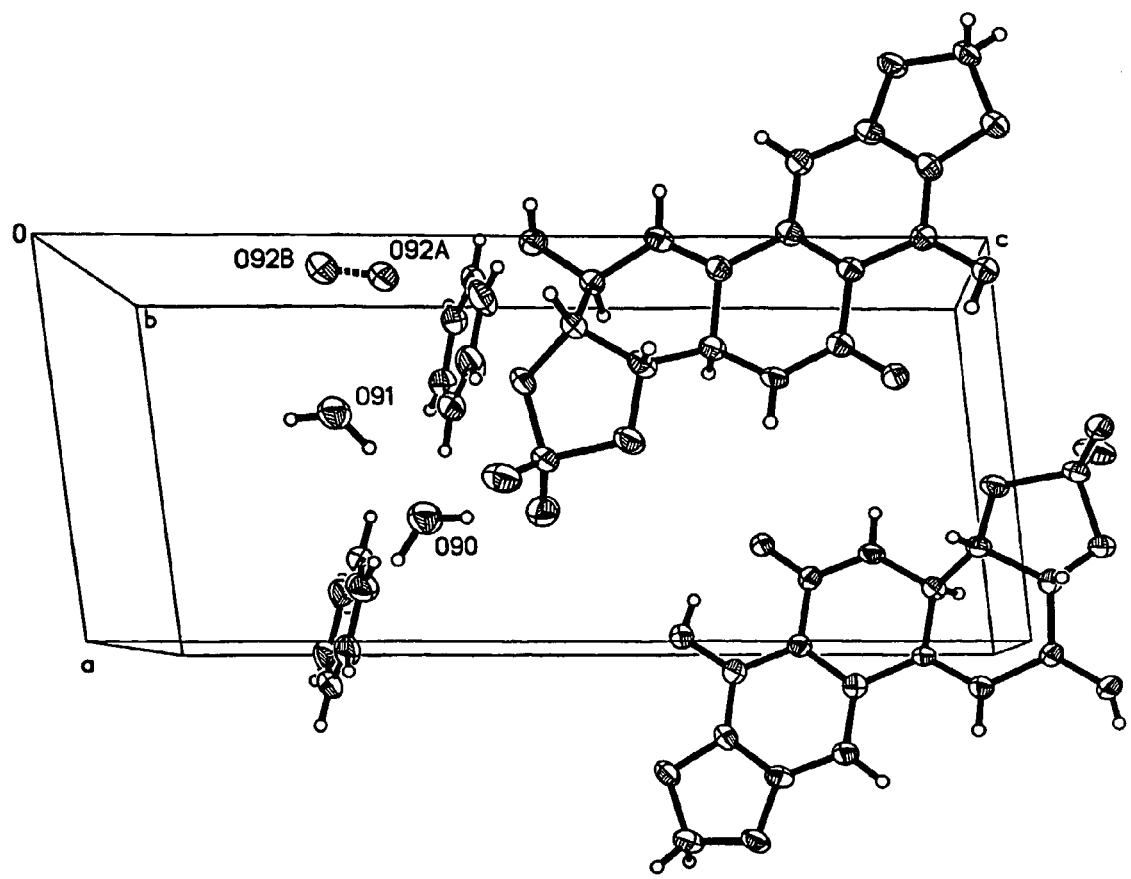
FIG. 2 illustrates the x-ray cell contents of pyridinium narcistatin hydrate (3a).
Figure 3:
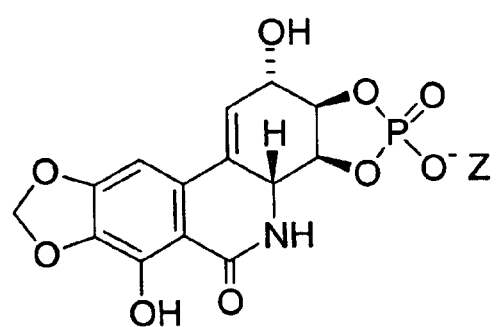
FIG. 3 illustrates the chemical structure of the narcistatin cyclic phosphate compounds of the invention.

Examination of the $^1$H-NMR (DMSO-$d_6$) spectrum of the pyridinium salt 3a showed a multiplet corresponding to the signals for four protons at 4.42-4.31 ppm and a doublet of doublets corresponding to the signal for one proton at 4.15 ppm. Assuming four ring hydrogens resonating in this region, the signal for H-1 was assigned downfield at 6.5 ppm. Only one of the signals corresponded to a hydroxyl group. A $D_2O$ experiment resulted in a considerable change in the splitting pattern of the multiplet at 4.3 ppm and 8.60 ppm, suggesting loss of the OH signal and NH-5 signal, respectively. Other signals at 13.66 and 9.00 were also absent from the $D_2O$ treated spectrum due to deuterium exchange with OH-7 and pyridinium NH. The $^{31}$P-NMR (DMSO-$d_6$) spectrum gave one signal at 20.3 ppm suggesting only one phosphorus atom, this together with the $^1$H NMR data suggested the formation of the cyclic phosphate. However, despite extensive 2D NMR experiments, the position of the phosphate could not be established unambiguously. Consequently, narciclasine pyridinium salt (3a) was recrystallized from pyridine-water and examined by X-ray crystallography to establish the 3,4-cyclic phosphate structure. The resulting structure of 3a is depicted in FIG. 1. In addition to two pyridinium cations and two cyclic phosphate anions, the unit cell was found to contain three molecules of water solvate, as shown in FIG. 2.

In order to extend the narcistatin cation series, phosphoric acid 3b was prepared by dissolving the pyridinium narcistatin in water and passing it through a column containing Dowex 50W X8 200 cation exchange resin (hydrogen form). A solution of the pyridinium narcistatin in water was also used to prepare the lithium (3c), sodium (3d) (procedure A), potassium (3e) and cesium (3f) salts of narcistatin by passage through a Dowex 50W X2 column bearing the respective cations. The magnesium (3g), calcium (3h), zinc (3*i*), and manganese (3j) salts were obtained by suspending phosphoric acid 3b in methanol-water (3:2) and adding 0.5 equivalent of the respective metal acetate in water. The resulting opaque solution was stirred for several days as the salt precipitated from solution. These dication salts proved to be only sparingly soluble in water. A selection of ammonium salts were prepared by allowing phosphoric acid 3b to react with the respective amine (1.2 equiv) at room temperature. The reaction mixture was concentrated and product precipitated to give ammonium salts 3k-o. Procedure B for the preparation of sodium narcistatin 3d is as follows. The reaction between narciclasine, tetrabutylammonium dihydrogen phosphate and DCCI in pyridine was carried out at 80° C. without the addition of the para-toluene sulfonic acid. The reaction was monitored by $^1$H NMR and found to go to completion in four days with addition of more reagents at 24 hours. Isolation followed by cation exchange chromatography gave sodium narcistatin in high yield (88%).

Narciclasine cyclic phosphate prodrugs 3a-*o* were evaluated against a minipanel of human cancer cell lines and the murine P388 lymphocytic leukemia. Results of the cancer cell line evaluation of narcistatins 3a-*o* appears in Table 1. The $GI_{50}$ 0.1-0.02 µg/ml strong activity range parallels that already reported for the parent, narciclasine (1). (Pettit, G. R.; Melody, N.; Herald, D. L. J. Org. Chem. 2001, 66, 2583-2587.)

Experimental Section.

Narciclasine (1) was isolated form *Hymenocallis littoralis* (Jacq.) Salisb, (Amaryllidaceae) grown by our group in Tempe, Ariz. (Pettit, G. R., et al., J. Nat. Prod. 1995, 58, 756-759; Pettit, G. R., et al., J. Nat. Prod. 1995, 58, 37-43.) Reagents were purchased from Aldrich Chemical unless otherwise noted and used as received. Solvents were distilled prior to use and pyridine preceding distillation was dried over potassium hydroxide pellets. Dowex 50×8-200 and Dowex 50WX2 cation exchange resins ($H^+$ form) were washed with methanol, 1 N hydrochloric acid and deionized water. The cation forms of the resin were obtained by washing with a 1 N solution of the appropriate base followed by deionized water. DEAE SEPHADEX A-25 weak anion exchange resin (acetate form) was purchased from the Sigma-Aldrich Company and was washed with 1 N triethylammonium bicarbonate (TEAB) solution and then equilibrated with 10 mN TEAB buffer solution.

Melting points were determined on a Fisher-Johns melting point apparatus and are uncorrected. Thin layer chromatography was performed on Analtech silica gel GHLF plates, the narciclasine containing derivatives were visible as green-blue fluorescent spots under long wave ultraviolet light, and were rendered permanent by staining with iodine vapor. Phosphorous containing compounds were detected using the modified Jungnickel's reagent (perchloric acid—malachite green—sodium molybdate) developed by Vaskovsky and Latshev. (Khorana, H. G., et al., A. R. J. Chem. Soc. 1953, 2257-2260; Khorana, H. G., J. Amer. Chem. Soc. 1954, 76, 3517-3527; Dekker, C. A., et al., H. G. J. Amer. Chem. Soc. 1954, 76, 3522-3527; Tener, G. M., et al., J. Amer. Chem. Soc. 1955, 77, 5348.) Optical rotation values were recorded using a Perkin Elmer 241 polarimeter. High resolution FAB spectra were obtained using a JEOL LCMate magnetic sector instrument in either the FAB mode, with a glycerol matrix, or by APCI with a polyethylene glycol reference. All $^1H$ NMR spectra were obtained using a Varian Gemini 300 MHz instrument unless otherwise noted. The $^{13}C$, $^1H$-$^1H$ COSY, $^1H$-$^{13}C$ HMBC, $^1H$-$^{13}C$ HMQC, and $^{31}P$-NMR experiments were conducted employing a Varian Unity 500 MHz instrument.

Pyridinium Narcistatin (3a)

Narciclasine 1 (1.0 g, 3.4 mmol) was added to pyridine (50 ml) and the solution was heated to 80° C. Next, tetrabutylammonium-dihydrogen phosphate (5.13 g, 15.11 mmol, 4.4 equiv), dicyclohexylcarbodiimide (5.0, 24.5 mmol, 7.0 equiv) and p-toluenesulfonic acid (3.0 g, 15.8 mmol, 4.63 equiv, added slowly) were added. After 2 g of the sulfonic acid was added, a precipitate began to separate. The reaction mixture was stirred under argon at 80° C. for 2.5 hours. The precipitate was collected and washed with methanol to remove pyridine. The precipitated cyclic phosphate (3a) was separated from the DCU by washing with water (200 ml). The aqueous filtrate was concentrated to an off-white solid and dried (vacuum) overnight to yield 0.59 g, 40.4%. The mother liquor was concentrated to a brown oil and water (750 ml) added. An immediate precipitate was observed, which was collected and dried to 0.75 g of white solid. The $^1H$ NMR (DMSO-$d_6$) showed this material to be recovered starting material with a small amount of DCU impurity. Recrystallization of phosphate 3a from pyridine-water gave crystals that were used for X-ray crystallography. $[\alpha]^{26}$=−6.4° (c 0.44, DMSO); m.p. 275° C.; $^1H$ NMR (DMSO-$d_6$, 500 MHz) δ13.66 (s, 1H), 9.00 (s, 1H), 8.60 (m, 3H), 7.9 (t, J=7.5Hz, 1H), 7.5 (m, 2H), 7.04 (s, 1H), 6.5 (s, 1H), 6.06 (d, J=3 Hz, 2H), 4.42-4.31 (m, 4H), 4.15 (dd, J=6.5 Hz, 1H); $^{13}C$ NMR (DMSO, 500 MHz) δ167.7, 152.6, 148.6(2), 145.2, 137.4(2), 133.5, 128.5, 126.9, 125.3, 124.4, 104.3, 102.1, 94.3, 76.9, 76.7, 70.4, 53.9; $^{31}P$ (DMSO-$d_6$, 200 MHz) 20.3 (s, 1P); found by HRAPCl (negative ions) mass spec. 368.0179, calc. for $C_{14}H_{11}O_9NP$ 368.2164.

Crystal Structure of Pyridinium Narcistatin (3a).

X-Ray Crystal Structure Determination. Pyridinium narcistatin hydrate (3a): A thin plate (~0.07×0.35×0.54 mm), grown from pyridine/water solution, was mounted on the tip of a glass fiber. Cell parameter measurements and data collection were performed at 123 K with a Bruker SMART 6000 diffractometer system using Cu Kα radiation. A sphere of reciprocal space was covered using the multirun technique. SMART for Windows NT v5.605; BrukerAXS Inc.: Madison, Wis., 2000. Thus, six sets of frames of data were collected with 0.396° steps in ω, and a last set of frames with 0.396° steps in φ, such that 91.7% coverage of all unique reflections to a resolution of 0.84A was accomplished.

Crystal Data: $C_{14}H_{11}NO_9P·C_5H_6N·1½H_2O$ (hydrate), $M_r$=475.34, triclinic, P1̄, a=7.4949(1), b=8.0371(1), c=16.9589(2) A, α=85.248(1), β=83.243(1), γ=79.383(1)°, V=994.60(2) $A^3$, Z=2, $\rho_c$=1.577 $Mg/m^3$, μ(CuKα)=1.837 $mm^{-1}$, λ=1.54178 A, F(000)=494.

A total of 7587 reflections was collected, of which 4733 reflections were independent reflections (R(int)=0.0273). Subsequent statistical analysis of the data set with the XPREP program indicated the spacegroup was P1̄. XPREP—The automatic space group determination program in the SHELXTL. (SHELXTL-NT Version 5.10; BrukerAXS Inc., Madison, Wis., 1997: an integrated suite of programs for the determination of crystal structures from diffraction data. This package includes, among others, XPREP (an automatic space group determination program), SHELXS (a structure solution program via Patterson or direct methods), and SHELXL (structure refinement software)). Final cell constants were determined from the set of the 4564 observed (>2σ(I)) reflections which were used in structure solution and refinement. An absorption correction was applied to the data with SADABS. (Blessing, R., Acta Crystallogr. 1995, A51, 33-38.) Structure determination and refinement was readily accomplished with the direct-methods program SHELXTL. (SHELXTL-NT Version 5.10; Bruker AXS Inc.: Madison, Wis., 1997.) An integrated suite of programs for the determination of crystal structures from diffraction data. This package includes, among others, XPREP (an automatic space group determination program), SHELXS (a structure solution program via Patterson or direct methods), and SHELXL (structure refinement software). All non-hydrogen atom coordinates were located in a routine run using default values for that program. The remaining H atom coordinates were calculated at optimum positions, except for water hydrogen atoms, which were located via difference maps. All non-hydrogen atoms were refined anisotropically in a full-matrix least-squares refinement procedure. The H atoms were included, their Uiso thermal parameters fixed at either 1.2 or 1.5 (depending on atom type) the value of the Uiso of the atom to which they were attached and forced to ride that atom. The final standard residual $R_1$ value for 3a was 0.0393 for observed data and 0.0403 for all data. The goodness-of-fit on $F^2$ was 1.053. The corresponding Sheldrick R values were $wR_2$ of 0.1074 and 0.1099, respectively. The final model used for pyridinium narcistatin 3a is shown in FIG. 1. In addition to the parent molecules (i.e., two narcistatin anions and two pyridinium cations) in the unit cell, three molecules of water solvate were also present. One of these water molecules was disordered over two sites, each of which were given 0.5 site occupancies. A final difference Fourier map showed minimal residual electron density; the largest difference peak and hole being +0.350 and −0.255 $e/A^3$, respectively. Final bond distances and angles were all within expected and acceptable limits.

Narcistatin (3b).

A solution of pyridinium narcistatin (3a, 0.05 g) in water (2 ml) was obtained by heating (water bath) at 60° C. The solution was allowed to cool prior to passing through a column prepared from Dowex 50×8-200 cation exchange resin (hydrogen form). A suspension began to form in the column as the phosphoric acid (3b) formed. The column was eluted with water and phosphoric acid 3b eluted as a milky white suspension. The combined fractions containing phosphoric acid 3b were freeze dried to afford the product as a colorless solid, (36 mg, 86%); m.p. 175° C. (dec.); $^1$H NMR (DMSO-$d_6$, 300 MHz), $\delta$13.65 (s, 1H), 9.02 (s, 1H), 7.06 (s, 1H), 6.48 (s, 1H), 6.17 (d, $J_{ab}$=10.2 Hz, 1H), 6.06 (m, 2H), 4.46-4.30 (m, 3H), 4.18 (m, 1H); calc for $C_{14}H_{13}NO_9P$ 370.0328; found by HR (APCI) [M+H]$^+$370.0361.

General Procedure for Preparation of Narcistatin Prodrugs 3c-f.

Pyridinium narcistatin (3a, 50 mg) was dissolved in water (35 ml) and the solution passed through a column (1×20 cm) of Dowex 50W-X2 bearing the respective cation. The u.v. active fractions were combined and freeze dried to give the corresponding narcistatin salt as a colorless solid unless otherwise recorded. The solubility of each in water (mg/ml) now follows: 3c, >50 mg; 3d, 60 mg; 3e, 11 mg; 3f, <13 mg.

Lithium Narcistatin (3c).

Yield, 65 mg, 77%; m.p. 220° C. (dec); $^1$H NMR (DMSO-$d_6$, 500 MHz) $\delta$ 13.79 (s, 1H), 8.71 (s, 1H), 7.07 (s, 1H), 6.49 (s, 1H), 6.13 (m, 2H), 4.36 (m, 2H), 4.04 (m, 1H), 3.93 (m, 1H); $^{13}$C NMR (DMSO-$d_6$, 300 MHz), 167.6, 152.5, 145.2, 133.3, 129.1, 127.3, 125.6, 104.3, 101.9, 94.2, 75.2, 74.6, 70.4, 53.8.

Sodium Narcistatin (3d). (Procedure A).

Colorless solid, 38 mg, 87%); $[\alpha]^{25}{}_D$=−6.33 (c 0.3, DMSO); m.p. 275° C.; $^1$H NMR (DMSO-$d_6$, 500 MHz) $\delta$ 13.72 (s, 1H) 8.63 (s, 1H), 6.99 (s, 1H), 6.41 (s, 1H), 6.05 (m, 2H), 5.77 (bs, 1H), 4.26 (m, 2H), 3.4 (m, 1H), 3.83 (m, 1H); $^{13}$C NMR (DMSO-$d_6$, 500 MHz), 167.6, 152.5, 145.2, 133.3, 129.1, 127.3, 125.5, 104.3, 101.9, 94.2, 75.2, 74.5, 70.4, 53.9; $^{31}$P (DMSO-$d_6$, 200 MHz) 16.98.

Sodium Narcistatin (3d). Procedure B.

Narciclasine 1 (0.113 g, 0.368 mmol) was added to pyridine (4 ml) and the solution heated to 80° C. Next, tetrabutylammonium dihydrogen phosphate (0.075 g, 0.22 mmol, 0.6 equiv.) and dicyclohexylcarbodiimide (0.4 g, 1.93 mmol, 5 equiv.) were added. The reaction mixture was stirred under argon at 80° C. for 24 hours. Tetrabutylammonium dihydrogen phosphate (0.185 g) was added followed by DCCI (0.4 g) and the reaction stirred for a further 72 hours. $^1$HNMR (DMSO-$d_6$) of the crude reaction mixture showed complete conversion to product. The reaction was cooled and filtered. Water (100 ml) was added to the mother liquor, which was then filtered to remove any precipitated DCU. The aqueous solution was then concentrated to minimum volume. The solution was then eluted on an ion exchange column of Dowex 50WX8-200 (sodium form) and the UV active fractions were combined and freeze dried to afford the product as a white solid (0.113 mg, 88%). Comparison of the $^1$HNMR of this product in DMSO-$d_6$ with the narcistatin sodium salt 3d prepared from the pyridinium narcistatin 3a by the method outlined above showed them to be identical. This method is more practical and dramatically improves the yield of narcistatin from narciclasine.

Potassium Narcistatin (3e)

Off-white solid, 59 mg, 80%, m.p. 250° C., $^1$H NMR (DMSO-$d_6$, 300 MHz) $\delta$ 13.74 (s, 1H), 8.65 (s, 1H), 6.98 (s, 1H), 6.40 (s, 1H), 6.04 (d, $J_{ab}$=2.4 Hz, 2H), 5.74 (bs, 1H), 4.25 (m, 2H), 3.9 (m, 1H), 3.78 (m, 1H).

Cesium Narcistatin (3f)

Off white solid, 51 mg, 91%, m.p. 245°C.; $^1$H NMR (DMSO-$d_6$, 300 MHz) $\delta$ 13.74 (s, 1H), 8.65 (s, 1H), 6.98 (s, 1H), 6.40 (s, 1H), 6.04 (m, 2H), 5.74 (bs, 1H), 4.25 (m, 2H), 3.92 (m, 1H), 3.79 (m, 1H).

An alternative method was also developed to isolate yield narcistatin sodium salt 3d. Narciclasine, tetrabutylammonium dihydrogen phosphate, DCCI and pyridinium p-toluene sulfonate were allowed to react at room temperature for 2 days. The reaction was monitored by t.l.c. using the solvent system 4:3:2:1 butanol-methanol-water-concentrated aqueous ammonia. Two major fluorescent spots were evident, narciclasine at $R_f$ 0.65 and product at a higher $R_f$ 0.69. Even after 4 days of stirring, the reaction was incomplete. The reaction mixture was added to water, the DCU collected, the mother liquor was evaporated to half its volume, and 2N aqueous ammonia was added at regular intervals to maintain a pH of 8-9. The solution was passed through a column (15×15 cm) of Dowex 50 (pyridinium form) in order to remove the unreacted narciclasine. Narciclasine remained bound to the resin while the charged phosphate passed through unchanged. The column was then washed with methanol and the unreacted narciclasine was recovered. The cyclic phosphate was separated from contaminating inorganic phosphate by anion exchange chromatography using DEAE-Sephadex and gradient elution with aqueous triethyl ammonium bicarbonate. The triethyl ammonium salt was converted to the sodium salt by passage through a Dowex 50 column (Na$^+$ form). A $^{31}$P-NMR confirmed the presence of a phosphate group. The yield from this reaction was 43%. Comparison of the $^1$H NMR of this product in $D_2O$ with the narcistatin sodium salt 3d prepared from the pyridinium narcistatin 3a by the method outlined above showed them to be identical. However, this method proved less practical and did not significantly improve the yield.

General Procedure for Preparation of Narcistatin Divalent Cation Salts 3g-j.

The experiment leading to magnesium salt 3g provides the general method and relative quantities of reactants and solvents. In each case, the respective metal acetate was employed.

Magnesium Narcistatin (3g)

To a mixture of phosphoric acid (3b, 50 mg, 0.135 mmol) and methanol-water (3:2) was added a solution of magnesium acetate (15 mg, 0.0675 mmol. 0.5 equiv) in water (1 ml). The mixture became opaque immediately upon addition of the metal acetate and was stirred for 3 days while further precipitation occurred. The solution was concentrated to a white residue and water-methanol was added (1.4 ml). The precipitate was collected and dried; grey solid, m.p. 210° C. dec. very insoluble in water, soluble in DMSO; $^1$H-NMR (DMSO-$d_6$, 300 MHz) $\delta$ 13.69 (s, 1H), 8.73 (s, 1H), 6.99 (s, 1H), 6.43 (s, 1H), 6.14 (m, 1H), 6.05 (s, 2H), 5.82 (bs, 1H), 4.41-4.31 (m, 2H), 4.03-3.95 (m, 2H). Each of the divalent cation salts proved to be only sparingly soluble in water.

Calcium Narcistatin (3h)

Grey solid; 30 mg, m.p. 195° C. (dec). $^1$H NMR (DMSO-$d_6$, 300 MHz), $\delta$ 13.68 (s, 1H), 8.69 (s, 1H), 7.0 (s, 1H), 6.43 (s, 1H), 6.14 (d, J=12.9 Hz, 1H), 6.05 (m, 2H), 4.29 (m, 2H), 4.02 (m, 1H), 3.94 (m, 1H).

Zinc Narcistatin (3i)

Yield of grey solid, 23 mg, m.p. 200° C. (dec). $^1$H NMR (DMSO-$d_6$, 300 MHz), $\delta$ 13.64 (s, 1H), 8.81 (s, 1H), 6.92 (s, 1H), 6.38 (s, 1H), 6.16 (m, 1H), 6.03 (s, 2H), 5.94 (bs, 1H), 4.31 (m, 2H), 4.20-4.17 (m, 1H), 4.07 (m, 1H).

Manganese Narcistatin (3j)

For this experiment, 41 mg of narcistatin (3b) was treated with manganese acetate (16 mg, 0.065 mmol. 0.5 equiv) in water (1 ml) to afford 35 mg of grey solid, m.p. 165° C. (dec); $^1$H NMR (DMSO-$d_6$, 300 MHz). The salt, while quite soluble in DMSO-$d_6$, did not give a useful spectrum.

General Procedure for Obtaining Ammonium Salts 3k-o.

Phosphoric acid 3b (0.25 g) was dissolved in methanol-dichloromethane-water (3:1:1) (10 ml). A 2 ml, aliquot of the phosphoric acid solution was added to each of the five flasks containing 1.2 equivalents of the respective amine and the reaction mixture stirred for 24 hr at rt. A precipitate separated from the reaction mixture with the quinine and imidazole examples. The solvent was concentrated and the residues reprecipitated from water-methanol to yield each of the ammonium salts 3k-o).

Quinidinium Narcistatin (3k).

Cream-colored solid; 34 mg, m.p. 205° C. (dec, 220° C. melts); $^1$H NMR (DMSO-$d_6$, 300 MHz), δ 13.71 (s, 1H), 8.68 (bs, 2H), 7.90 (d, J=8.4 Hz, 1H), 7.52 (s, 1H), 7.37-7.40 (m, 3H), 6.99 (s, 1H), 6.4 (s, 1H), 6.13-6.01 (m, 3H), 5.10 (m, 4H), 4.25 (m, 2H), 3.92 (m, 5H), 3.6-3.2 (m, 6H), 2.42 (m, 1H), 2.2-2.12 (m, 1H), 1.91-1.84 (m, 1H), 1.60 (m, 2H), 1.47-1.38 (m, 1H).

Quininium Narcistatin (3l).

Cream-colored solid; 55 mg, m.p. 195° C.; $^1$H NMR (DMSO-$d_6$, 300 MHz), δ 13.72 (s, 1H), 8.70 (bs, 2H), 7.93 (d, J=8.4 Hz, 1H), 7.57 (bs, 1H), 7.45-7.39 (m, 3H), 6.99 (s, 1H), 6.41 (s, 1H), 6.05 (m, 3H), 5.80-5.73 (m, 2H), 5.07-4.93 (m, 2H), 4.25 (bs, 2H), 4.03-3.85 (m, 5H), 3.38 (m, 6H), 1.91 (m, 4H), 1.71 (m, 1H), 1.47 (m, 1H).

Imidazolium Narcistatin (3m).

Off-white solid, 39 mg, m.p. 210° C.; $^1$H NMR (DMSO-$d_6$ 300 MHz), δ 13.73 (s, 1H), 13.4 (s, 1H), 8.71 (s, 1H), 8.06 (bs, 1H), 7.21 (bm, 2H), 6.98 (s, 1H), 6.41 (s, 1H), 6.11 (bs, 1H), 6.04 (m, 2H), 4.25 (m, 2H), 3.99 (m, 1H), 3.84 (m, 1H).

Morpholinium Narcistatin (3n).

Off-white solid, 20 mg, m.p. 230° C.; $^1$H NMR (DMSO-$d_6$ 300 MHz), δ 13.73 (s, 1H), 8.68 (s, 1H), 6.99 (s, 1H), 6.41 (s, 1H), 6.04 (d, J=2.7 Hz, 2H), 5.76 (bs, 1H), 4.25 (bm, 2H), 3.97 (m, 1H), 3.92-3.71 (m, 5H), 3.03 (m, 4H), 1.22 (s, 1H).

Piperazinium Narcistatin (3o).

Off-white solid, 21 mg, m.p. 270° C.; $^1$H NMR (DMSO-$d_6$ 300 MHz), δ 13.74 (s, 1H), 8.66 (s, 1H), 6.98 (s, 1H), 6.40 (s, 1H), 6.04 (d, J=1.8 Hz, 2H), 5.74 (bs, 1H), 4.24 (bm, 2H), 3.93 (m, 1H), 3.81 (m, 1H), 3.14 (s, 2H), 2.83 (s, 9H).

Administration

Dosages

The dosage of the presently disclosed compounds to be administered to humans and other animals requiring treatment will depend upon numerous factors, including the identity of the neoplastic disease; the type of host involved, including its age, health and weight; the kind of concurrent treatment, if any; the frequency of treatment and therapeutic ratio. Hereinafter are described various possible dosages and methods of administration, with the understanding that the following are intended to be illustrative only, and that the actual dosages to be administered, and methods of administration or delivery may vary therefrom. The proper dosages and administration forms and methods may be determined by one of skill in the art.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/k of host body weight.

Expressed in terms of concentration, an active ingredient can be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration.

The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal installation, a fluid unit dosage form is prepared utilizing an active ingredient and a suitable pharmaceutical vehicle, preferably purified (P.F.) water, a dry powder, can be formulated when insulation is the administration of choice.

For use as aerosols, the active ingredients can be packaged in a pressurized aerosal container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies one or more of the compounds described herein.

Composition "A"

Hard-Gelatin Capsules

One thousand two-piece hard gelatin capsules for oral use, each capsule containing 200 mg of an active ingredient are prepared from the following types and amounts of ingredients:

| Active ingredient, micronized | 200 g |
| --- | --- |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient, are prepared from the following types and amounts of ingredients:

| Active ingredient, micronized | 200 g |
| --- | --- |
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

A sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

One liter of a sterile aqueous suspension for intranasal instillation, containing 20 mg of an active ingredient in each milliliter, is prepared from the following types and amounts of ingredients:

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition "J"

Insulation

One hundred grams of an active ingredient in bulk form is finely divided by means of an air micronizer.

The foregoing composition is useful for treating a neoplastic disease, by the inhalation of 300 mg one to four times a day.

It is of course understood that such modifications, alterations and adaptations as will readily occur to the artisan confronted with this disclosure are intended within the spirit of the present invention.

TABLE 1

Solubilities, Human Cancer Cell Line and Murine P-388 Lymphocytic Inhibitory Activities of Cyclic Phosphates 3-16.

| Compound | Solubilities[a] (mg/ml) | ED$_{50}$ (µg/ml) Leukemia P388 | GI$_{50}$ (µg/ml) | | | | | |
|---|---|---|---|---|---|---|---|---|
| | | | Pancreas-a BXPC-3 | Breast MCF-7 | CNS SF 268 | Lung-NSC NCI-H460 | Colon KM20L2 | Prostate DU-145 |
| 3a | 7 | $1.91 \times 10^{-1}$ | $2.2 \times 10^{-1}$ | $2.7 \times 10^{-1}$ | $1.5 \times 10^{-1}$ | $2.7 \times 10^{-1}$ | $3.4 \times 10^{-1}$ | $1.7 \times 10^{-1}$ |
| 3b | 4 | $2.75 \times 10^{-1}$ | $3.3 \times 10^{-1}$ | $3.5 \times 10^{-1}$ | $2.2 \times 10^{-1}$ | $4.7 \times 10^{-1}$ | $5.3 \times 10^{-1}$ | $1.6 \times 10^{-1}$ |
| 3c | >50 | $1.21 \times 10^{-1}$ | $2.5 \times 10^{-1}$ | $3.1 \times 10^{-1}$ | $1.7 \times 10^{-1}$ | $3.0 \times 10^{-1}$ | $2.6 \times 10^{-1}$ | $1.3 \times 10^{-1}$ |
| 3d | 60 | $2.55 \times 10^{-1}$ | $3.2 \times 10^{-1}$ | $5.6 \times 10^{-1}$ | $2.3 \times 10^{-1}$ | >1 | $4.5 \times 10^{-1}$ | $1.2 \times 10^{-1}$ |
| 3e | 11 | $2.42 \times 10^{-1}$ | $3.6 \times 10^{-1}$ | $4.0 \times 10^{-1}$ | $1.9 \times 10^{-1}$ | $6.7 \times 10^{-1}$ | $5.6 \times 10^{-1}$ | $2.6 \times 10^{-1}$ |
| 3f | <13 | $1.83 \times 10^{-1}$ | $4.1 \times 10^{-1}$ | $6.2 \times 10^{-1}$ | $3.3 \times 10^{-1}$ | >1 | $6.6 \times 10^{-1}$ | $1.3 \times 10^{-1}$ |
| 3g | <1.5 | $1.70 \times 10^{-1}$ | $1.9 \times 10^{-1}$ | $2.5 \times 10^{-1}$ | $1.4 \times 10^{-1}$ | $2.9 \times 10^{-1}$ | $3.1 \times 10^{-1}$ | $1.0 \times 10^{-1}$ |
| 3h | <1 | $2.23 \times 10^{-1}$ | $4.5 \times 10^{-2}$ | $5.9 \times 10^{-2}$ | $3.1 \times 10^{-2}$ | $1.2 \times 10^{-1}$ | $5.9 \times 10^{-2}$ | $9.3 \times 10^{-3}$ |
| 3i | 1.7 | $2.87 \times 10^{-2}$ | $6.9 \times 10^{-2}$ | $1.4 \times 10^{-1}$ | $5.3 \times 10^{-2}$ | $2.1 \times 10^{-1}$ | $1.6 \times 10^{-1}$ | $1.6 \times 10^{-2}$ |
| 3j | <3 | $4.27 \times 10^{-2}$ | $4.9 \times 10^{-2}$ | $7.0 \times 10^{-2}$ | $4.0 \times 10^{-2}$ | $1.5 \times 10^{-1}$ | $1.3 \times 10^{-1}$ | $3.4 \times 10^{-2}$ |
| 3k | <1 | $2.71 \times 10^{-1}$ | $3.1 \times 10^{-1}$ | $5.0 \times 10^{-1}$ | $2.5 \times 10^{-1}$ | $7.7 \times 10^{-1}$ | $5.8 \times 10^{-1}$ | $2.2 \times 10^{-1}$ |
| 3l | <1 | $3.42 \times 10^{-1}$ | $5.1 \times 10^{-2}$ | $1.2 \times 10^{-1}$ | $4.5 \times 10^{-2}$ | $1.7 \times 10^{-1}$ | $1.2 \times 10^{-1}$ | $1.3 \times 10^{-2}$ |
| 3m | 5.8 | $2.40 \times 10^{-1}$ | $4.5 \times 10^{-1}$ | $9.0 \times 10^{-1}$ | $3.8 \times 10^{-1}$ | >1 | >1 | $4.4 \times 10^{-1}$ |
| 3n | >13 | $2.32 \times 10^{-1}$ | $2.5 \times 10^{-1}$ | $4.8 \times 10^{-1}$ | $2.4 \times 10^{-1}$ | >1 | $5.4 \times 10^{-1}$ | $1.4 \times 10^{-1}$ |
| 3o | 1.9 | $3.78 \times 10^{-2}$ | $1.0 \times 10^{-1}$ | $1.7 \times 10^{-1}$ | $9.9 \times 10^{-2}$ | $2.4 \times 10^{-1}$ | $2.2 \times 10^{-1}$ | $3.2 \times 10^{-2}$ |

[a]Solubility values were obtained using 1 ml distilled water at 25° C.

What is claimed is:

1. A compound having the following structure:

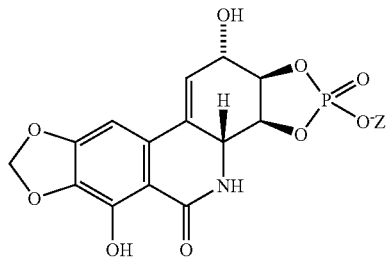

wherein Z is selected from the group consisting of pyridinium, H$^+$, Li$^+$, Na$^+$, K$^+$, Cs$^+$, Mg$^{2+}$, Ca$^{2+}$, Zn$^{2+}$, Mn$^{2+}$, quinidine, quinine, imidazole, morpholine and piperazine.

2. A pharmaceutical composition comprising the compound of claim 1 and a pharmaceutically acceptable carrier therefore.

3. A method for treating cancer selected from the group consisting of leukemia, pancreatic cancer, breast cancer, central nervous system cancer, lung cancer, colon cancer and prostate cancer, comprising administering to a human subject afflicted with cancer a pharmaceutically effective amount of the compound:

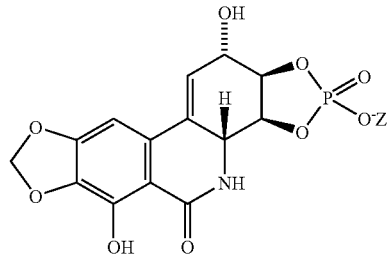

wherein Z is selected from the group consisting of pyridinium, H$^+$, Li$^+$, Na$^{30}$, K$^+$, Cs$^+$, Mg$^{2+}$, Ca$^{2+}$, Zn$^{2+}$, Mn$^{2+}$, quinidine, quinine, imidazole, morpholine and piperazine.

* * * * *